(12) United States Patent
van Damme et al.

(10) Patent No.: US 6,855,539 B2
(45) Date of Patent: Feb. 15, 2005

(54) DEVICE FOR PERFORMING AN ASSAY, A METHOD FOR MANUFACTURING SAID DEVICE, AND USE OF A MEMBRANE IN THE MANUFACTURE OF SAID DEVICE

(75) Inventors: Hendrik Sibolt van Damme, s'-Hertogenbosch (NL); Hermanus Johannes Maria Kreuwel, Schijndel (NL); Tim Kievits, Vught (NL); Marinus Gerardus Johannus van Beuningen, Oss (NL); Pieter Jacob Boender, Nijmegen (NL)

(73) Assignee: PamGene International B.V., 's-Hertogenbosch (NL)

( * ) Notice: Subject to any disclaimer, the term of this patent is extended or adjusted under 35 U.S.C. 154(b) by 223 days.

(21) Appl. No.: 09/997,213

(22) Filed: Nov. 27, 2001

(65) Prior Publication Data

US 2002/0164584 A1 Nov. 7, 2002

Related U.S. Application Data

(63) Continuation-in-part of application No. 09/843,929, filed on Apr. 30, 2001, now Pat. No. 6,635,493, which is a continuation of application No. 09/403,559, filed as application No. PCT/EP98/04938 on Jul. 7, 1998, now Pat. No. 6,225,131.

(30) Foreign Application Priority Data

Jul. 11, 1997 (EP) ............................................ 97202140

(51) Int. Cl.$^7$ ................................................ C12M 1/34
(52) U.S. Cl. ........................ 435/287.2; 422/57; 422/58; 435/5; 435/6; 435/7.1; 435/287.1; 436/518; 436/524; 436/810
(58) Field of Search ........................ 422/57, 58; 435/5, 435/6, 7.1, 287.1, 287.2, 810; 436/518, 524

(56) References Cited

U.S. PATENT DOCUMENTS

| 3,652,761 A | 3/1972 | Weetall et al. |
|---|---|---|
| 3,671,410 A | 6/1972 | Stahr |
| 4,427,415 A | 1/1984 | Cleveland |
| 4,693,985 A | 9/1987 | Degen et al. |
| 4,777,021 A | 10/1988 | Wetz et al. |
| 5,772,735 A | 6/1998 | Sehgal et al. |
| 5,843,767 A | 12/1998 | Beattie |
| 6,225,131 B1 * | 5/2001 | van Damme et al. ....... 436/524 |
| 6,635,493 B2 * | 10/2003 | van Damme et al. ....... 436/524 |

FOREIGN PATENT DOCUMENTS

| EP | 0 178 831 B1 | 7/1991 |
|---|---|---|
| GB | 1432713 | 4/1976 |
| WO | WO 95/11755 | 5/1995 |
| WO | WO 99/02266 | 1/1999 |

OTHER PUBLICATIONS

Socransky et al., "Checkerboard" DNA–DNA Hybridization. BioTechniques, 17(4):788–92, 1994.
Alderton et al., Automated DNA Hybridization. Analytical Biochemistry, 218:98–102, 1994.
Tonucci et al., Nanochannel Array Glass. Science, 258:783–85, Oct. 30, 1992.
Fadda et al., Covalent Coupling of a Concanavalin A to Commercial Alumina. Biotechnology and Applied Biochemistry, 16:221–27, 1992.
Rigby et al., An Anodizing Process for the Production of Inorganic Microfiltration Membranes. Trans. Inst. Metal Finish, 68(3):95–98, 1990.

* cited by examiner

*Primary Examiner*—Christopher L. Chin
(74) *Attorney, Agent, or Firm*—Amster, Rothstein & Ebenstein LLP

(57) ABSTRACT

Disclosed is a device useful for performing an assay comprising a substrate having interconnecting channels that open out onto a surface for sample application, the channels being provided in at least one cross-sectional area with a first binding substance capable of binding a particular analyte, the substrate being an electrochemically manufactured metal oxide membrane and containing the first binding substance within the through-going channels. Similar devices are also useful for chemical synthesis. Assay and chemical synthesis methods are also disclosed, as are kits for performing the assays or chemical syntheses.

21 Claims, 4 Drawing Sheets

SEQUENCE LISTING

<160> NUMBER OF SEQ ID NOS: 21

<210> SEQ ID NO 1
<211> LENGTH: 145
<212> TYPE: RNA
<213> ORGANISM: Human immunodeficiency virus type 1

<400> SEQUENCE: 1
cccugcuaug ucacuucccc uugguucucu caucuggccu ggugcaauag gcccugcaug      60
cacuggaugc acucuauccc auucugcagc uuccucauug auggucucuu uuaacauuug     120
cauggcugcu ugaugucccc ccacu                                           145

<210> SEQ ID NO 2
<211> LENGTH: 145
<212> TYPE: RNA
<213> ORGANISM: Human immunodeficiency virus type 1

<400> SEQUENCE: 2
cccugcuaug ucacuucccc uugguucucu caucuggccu ggugcaauag gcccugcaug      60
cgacugucau cuaucuacac ugucugcagc uuccucauug auggucucuu uuaacauuug     120
cauggcugcu ugaugucccc ccacu                                           145

<210> SEQ ID NO 3
<211> LENGTH: 24
<212> TYPE: DNA
<213> ORGANISM: Human immunodeficiency virus type 1

<400> SEQUENCE: 3
gaatgggata gagtgcatcc agtg                                             24

<210> SEQ ID NO 4
<211> LENGTH: 24
<212> TYPE: DNA
<213> ORGANISM: Human immunodeficiency virus type 1

<400> SEQUENCE: 4
gacagtgtag atagatgaca gtcg                                             24

<210> SEQ ID NO 5
<211> LENGTH: 25
<212> TYPE: DNA
<213> ORGANISM: Human immunodeficiency virus type 1

<400> SEQUENCE: 5
tgttaaaaga gaccatcaat gagga                                            25

<210> SEQ ID NO 6

```
<211> LENGTH: 21
<212> TYPE: DNA
<213> ORGANISM: Artificial
<220> FEATURE:
<223> OTHER INFORMATION: probe A of Table 2

<400> SEQUENCE: 6
ttgtacagaa atggaaaagg a                                              21

<210> SEQ ID NO 7
<211> LENGTH: 21
<212> TYPE: DNA
<213> ORGANISM: Artificial
<220> FEATURE:
<223> OTHER INFORMATION: Probe B of Table 2

<400> SEQUENCE: 7
ttgtgcagag atggaaaagg a                                              21

<210> SEQ ID NO 8
<211> LENGTH: 21
<212> TYPE: DNA
<213> ORGANISM: Artificial
<220> FEATURE:
<223> OTHER INFORMATION: Probe C of Table 2

<400> SEQUENCE: 8
ttgtaaagaa atggaacagg a                                              21

<210> SEQ ID NO 9
<211> LENGTH: 21
<212> TYPE: DNA
<213> ORGANISM: Artificial
<220> FEATURE:
<223> OTHER INFORMATION: Probe E of Table 2

<400> SEQUENCE: 9
ttgcacagaa atggaaaagg a                                              21

<210> SEQ ID NO 10
<211> LENGTH: 21
<212> TYPE: DNA
<213> ORGANISM: Artificial
<220> FEATURE:
<223> OTHER INFORMATION: Probe G of Table 2

<400> SEQUENCE: 10
ttgtacagaa ctggaaaagg a                                              21

<210> SEQ ID NO 11
<211> LENGTH: 21
<212> TYPE: DNA
<213> ORGANISM: Artificial
<220> FEATURE:
<223> OTHER INFORMATION: Probe H of Table 2

<400> SEQUENCE: 11
ttgtttagaa atggaaaagg a                                              21

<210> SEQ ID NO 12
<211> LENGTH: 21
<212> TYPE: DNA
<213> ORGANISM: Artificial
<220> FEATURE:
<223> OTHER INFORMATION: Probe I of Table 2

<400> SEQUENCE: 12
```
ttgtgcattt atggaggagg a                                                    21

<210> SEQ ID NO 13
<211> LENGTH: 21
<212> TYPE: DNA
<213> ORGANISM: Artificial
<220> FEATURE:
<223> OTHER INFORMATION: Probe J of Table 2

<400> SEQUENCE: 13
ttgtgcagaa atggaaaagg a                                                    21

<210> SEQ ID NO 14
<211> LENGTH: 21
<212> TYPE: DNA
<213> ORGANISM: Artificial
<220> FEATURE:
<223> OTHER INFORMATION: Probe K of Table 2

<400> SEQUENCE: 14
ttgtacagaa atcgaaaagg a                                                    21

<210> SEQ ID NO 15
<211> LENGTH: 21
<212> TYPE: DNA
<213> ORGANISM: Artificial
<220> FEATURE:
<223> OTHER INFORMATION: Probe L of Table 2

<400> SEQUENCE: 15
ccattgacag aagaaaaaat a                                                    21

<210> SEQ ID NO 16
<211> LENGTH: 21
<212> TYPE: DNA
<213> ORGANISM: Artificial
<220> FEATURE:
<223> OTHER INFORMATION: Probe M of Table 2

<400> SEQUENCE: 16
ttaataagag aactcaagac t                                                    21

<210> SEQ ID NO 17
<211> LENGTH: 21
<212> TYPE: DNA
<213> ORGANISM: Artificial
<220> FEATURE:
<223> OTHER INFORMATION: Probe N of Table 2

<400> SEQUENCE: 17
ttgtaaagag atggaacagg a                                                    21

<210> SEQ ID NO 18
<211> LENGTH: 21
<212> TYPE: DNA
<213> ORGANISM: Artificial
<220> FEATURE:
<223> OTHER INFORMATION: Probe O of Table 2

<400> SEQUENCE: 18
ttgtacagag atggaaaagg a                                                    21

<210> SEQ ID NO 19
<211> LENGTH: 21
<212> TYPE: DNA

```
-continued

<213> ORGANISM: Artificial
<220> FEATURE:
<223> OTHER INFORMATION: Probe P of Table 2

<400> SEQUENCE: 19
ttgtacagaa atggagaagg a                                        21

<210> SEQ ID NO 20
<211> LENGTH: 21
<212> TYPE: DNA
<213> ORGANISM: Artificial
<220> FEATURE:
<223> OTHER INFORMATION: Probe Q of Table 2

<400> SEQUENCE: 20
ttgtacagaa ctggagaagg a                                        21

<210> SEQ ID NO 21
<211> LENGTH: 21
<212> TYPE: DNA
<213> ORGANISM: Artificial
<220> FEATURE:
<223> OTHER INFORMATION: Probe R of Table 2

<400> SEQUENCE: 21
ttgtacagaa ttggaaaagg a                                        21
```

DEVICE FOR PERFORMING AN ASSAY, A METHOD FOR MANUFACTURING SAID DEVICE, AND USE OF A MEMBRANE IN THE MANUFACTURE OF SAID DEVICE

CROSS-REFERENCE TO RELATED APLICATIONS

This application is a continuation-in-part of U.S. patent application Ser. No. 09/843,929, filed Apr. 30, 2001, now U.S. Pat. No. 6,635,493, which is a continuation of U.S. Patent Application 09/403,559, filed Oct. 25, 1999, now U.S. Pat. No. 6,225,131, which is a filing under 35 U.S.C. §371 of PCT/EP98/04938, filed Jul. 7, 1998, which claims priority to European Patent Application 97202140, filed Jul. 11, 1997.

The present invention relates to a device for performing an assay, which device comprises a substrate having oriented through-going channels, said channels opening out on a surface for sample application, the channels in at least one area of the surface for sample application being provided with a first binding substance capable of binding to an analyte.

BACKGROUND OF THE INVENTION

Such a device is disclosed in WO95/11755 for "sequencing by hybridisation" applications. The device comprises a substrate provided with channels, the channels being oriented substantially perpendicular to the surface of the substrate. Three types of substrate are disclosed. The first type is comprised of a multitude of hollow glass fibres. It is manufactured by stacking glass fibres having an etchable core, providing the stack with flat ends, polishing those ends, and etching the cores, usually with acid. The second type of substrate is produced by electrochemical etching of a crystalline silicon wafer. First, the position of the channels as well as their size are defined using standard photolithographic methods. Subsequently the oriented channels are formed electrochemically. The third type of substrate is produced by nuclear track etching of an inorganic substrate. This method, comprising the steps of exposing the substrate to heavy, energetic charged particles and wet-etching, results in a substrate with channels scattered randomly over the surface of the substrate. With higher pore densities and porosity there is more chance of fusion of channels, which show reduced flow resistance with respect to other, non-fused channels.

All three types of substrates are quite expensive because of the labour-intensive manufacturing processes and/or expensive starting materials and wasteful operations, such as sawing and polishing, and/or expensive equipment. In addition, the substrates are characterized by a relatively low porosity of 30% and more. More advantageous, higher porosities of up to 80% are said to be achievable, but only at relatively low channel densities, with the disadvantage that the effective surface area of the channels of a particular area of the substrate is lower in comparison with a substrate having a comparable porosity but with higher channel densities (and consequently narrower channels).

A further disadvantage of the silicon-based substrates as disclosed in WO 95/11755 is that they are not transparent for light. These substrates therefore prohibit the advantageous use of optical marker systems for the detection of analyte bound in the substrate. Popular optical marker systems are for instance based on enzymatically induced colour (including infrared or ultraviolet) reactions, or capable of bio- or chemiluminescence, or photoluminescence, including fluorescence. In the latter case both the excitation light and emitted luminescent light have to pass through the substrate material.

SUMMARY OF THE INVENTION

The object of the present invention is to overcome the above disadvantages and provide a substrate having both a high channel density and a high porosity, allowing even higher density arrays comprising different first binding substances per unit of the surface for sample application. In addition, the substrate is highly transparent for UV, visible and IR light. More in particular, the object of the present invention is to provide a device comprising a relatively cheap substrate that does not require the use of any typical microfabrication technology and, that offers an improved control over the liquid distribution over the surface of the substrate.

The above objects are achieved with a device wherein the porous substrate is an electrochemically manufactured metal oxide membrane.

Metal oxide membranes having through-going, oriented channels can be manufactured cheaply through electrochemical etching of a metal sheet. Metals considered are, among others, tantalum, titanium, and aluminium, as well as alloys of two or more metals and doped metals and alloys. The metal oxide membranes are transparent, especially if wet, which allows for assays using optical techniques to be combined with the control of liquid and therefore creating the ability to monitor binding as a function of time and temperature. Such membranes have oriented channels with well controlled diameter and advantageous chemical surface properties. Additionally, the channels of the metal oxide membranes of the present invention are interconnected, which can provide improved porosity over membranes with unconnected channels.

One of the major advantages of the device of the invention is the possibility of following the results of incubating the first binding substance and analyte as a function of time. This is illustrated in Examples 5 and 6.

The invention thus provides a device for performing an assay. The device comprises a substrate having interconnected channels, wherein the channels open out on a surface for sample application. The channels in at least one area of the surface for sample application are provided with a first binding substance capable of binding to an analyte, wherein the substrate is an electrochemically manufactured metal oxide membrane and the first binding substance is within the interconnected channels in the substrate. In preferred embodiments, the metal oxide membrane is comprised of aluminium oxide. In some embodiments, the first binding substance is covalently bound to the substrate.

Preferably, the first binding substance is selected from the group consisting of an oligopeptide, a polypeptide, an oligonucleotide, a polynucleotide, a hapten, and a ligand for a receptor. When the first binding substance is an oligopeptide, the oligopeptide can comprise an immunogenic epitope, for example a portion of an HIV protein. When the first binding substance is a polypeptide, the polypeptide can be, for example, an antibody or an enzyme. When the first binding substance is an oligonucleotide, a preferred example is a portion of an HIV genome.

In additional embodiments, the invention is directed to a method of manufacturing the above device, wherein the first binding substance is synthesised in situ. The in situ synthesis can be done chemically or enzymatically. The compound for synthesising the first binding substance can be applied to a particular area using ink-jet technology, preferably using electrostatic attraction. Ink-jet technology, preferably using electrostatic attraction, can also be used to apply the first binding substance per se.

The present invention is also directed to a kit comprising any of the above devices along with a detection means for determining whether binding has occurred between the first binding substance and the analyte. Preferred detection means for these kits is a second binding substance provided with a label. Preferably, the label is capable of inducing a colored or infrared or ultraviolet reaction product, or capable of bio- or chemo- or photoluminescence. In other preferred embodiments, the detection means uses an enzymatic reaction.

Additionally, the present invention is directed to a method for the detection of an analyte in a sample, the method comprising the steps of a) contacting the sample with any of the above-described devices, b) allowing binding to take place between the first binding substance and the analyte to be detected, and c) detecting whether binding has occurred between first binding substance and the analyte. In certain aspects of these embodiments, step a) and b) is repeated at least once before performing step c), preferably by first performing step a) and b) by passing the sample through the membrane in one direction perpendicular to the surface of the membrane, then repeating steps a) and b) by passing the sample through the membrane in the opposite direction.

In these methods, preferred analytes comprise a polynucleotide or oligonucleotide. A preferred polynucleotide is a portion of an HIV genome. The detection step in these methods can comprise the use of a molecular beacon or any other suitable probe.

These methods can also be used in oligonucleotide or polynucleotide sequencing. In those applications, the results of step c) are used to determine sequence information of the polynucleotide or oligonucleotide.

These assay methods are also useful with an analyte that comprises a polypeptide. A preferred polypeptide is one from an HIV.

The invention is also directed to a method for the detection of an analyte in a sample. The method comprises the steps of a) contacting the sample with a device, which device comprises a substrate having through-going channels, said channels opening out on a surface for sample application, the channels in at least one area of the surface for sample application being provided with a first binding substance capable of binding to an analyte, wherein the first binding substance is within the through-going channels in the substrate; b) passing the sample through the membrane in one direction perpendicular to the surface of the membrane in a manner sufficient to allow binding to take place between the first binding substance and the analyte to be detected; c) repeating steps a) and b) by passing the sample through the membrane in the opposite direction; and d) detecting whether binding has occurred between the first binding substance and the analyte. In preferred embodiments of these methods, steps a), b) and c) are repeated at least once before performing step d). The analyte in these methods can comprise a polynucleotide or an oligonucleotide. In some embodiments, the polynucleotide or oligonucleotide comprises a portion of an HIV genome. In these methods, the results of step d) can be used to determine sequence information of the polynucleotide or oligonucleotide. In other embodiments, the analyte comprises a polypeptide, for example a polypeptide from an HIV.

The present invention is also directed to a device for performing a chemical synthesis. The device comprises a substrate having interconnected channels, said channels opening out on a surface and being oriented essentially perpendicular to the surface for reagent application. The channels in at least one area of the surface for reagent application are provided with a first reacting substance capable of reacting with a second reacting substance. In these devices, the substrate is an electrochemically manufactured metal oxide membrane and the first reacting substance is within the interconnected channels in the substrate. Preferably, the first reacting substance is a polymer, preferably covalently bound to the substrate. In other embodiments, the polymer is capable of covalently binding to an organic molecule of less than 1000 Dalton. In some aspects, the polymer is capable of covalently binding to a modified amino acid useful for oligopeptide synthesis. In other aspects, the polymer is capable of covalently binding to a modified nucleotide useful for oligonucleotide synthesis.

Additional embodiments are directed to methods of manufacturing the device for chemical synthesis described above. In those methods, the first reacting substance is applied to a particular area using ink-jet technology.

The invention is additionally directed to a method of synthesizing an oligopeptide. The method comprises the following steps: (a) contact the device for chemical synthesis described above with a protected amino acid under conditions and for a time sufficient for the protected amino acid to covalently bind to the polymer; (b) treat the device to remove the protecting group from the protected amino acid to form a device comprising a polymer covalently bound to a first amino acid; and (c) contact the device comprising a polymer covalently bound to a first amino acid with a second protected amino acid under conditions and for a time sufficient for the second protected amino acid to form a peptide bond with the first amino acid. These methods can utilize naturally occurring amino acids as well as amino acid analogs known in the art, such as peptide nucleic acids.

In a related application, the invention is directed to a method of synthesizing an oligonucleotide. The method comprises the following steps: (a) contact the device for chemical synthesis described above with a protected nucleotide under conditions and for a time sufficient for the protected nucleotide to covalently bind to the polymer; (b) treat the device to remove the protecting group from the protected nucleotide to form a device comprising a polymer covalently bond to a first nucleotide; and (c) contact the device comprising a polymer covalently bond to a first nucleotide with a second protected nucleotide under conditions and for a time sufficient for the second protected nucleotide to form a phosphodiester bond with the first nucleotide. The oligonucleotide in these methods can be an oligoribonucleotide or an oligodeoxyribonucleotide or analogs of these.

In other embodiments, the present invention is directed to a method of performing a chemical synthesis to create a desired chemical. The method comprises the following steps:

a) contacting a device comprising a first reacting substance with a second reacting substance, wherein the device comprises a substrate having interconnected channels, said channels opening out on a surface, the channels in at least one area of the surface for reagent application being provided with the first reacting substance capable of reacting with the second reacting substance to covalently attach the second reacting substance to the first reacting substance, wherein the substrate is an electrochemically manufactured metal oxide membrane and the first reacting substance is within the interconnected channels in the substrate;

b) incubating the device under conditions and for a time sufficient for the first reacting substance to react with the second reacting substance;

c) repeating steps a) and b) to covalently attach a third reacting substance to the first and second reacting substance;

d) repeating step c) if necessary with a fourth reacting substance and subsequent reacting substances until the chemical synthesis is complete and the desired chemical is within the interconnected channels in the substrate; and e) cleaving the desired chemical from the interconnected channels in the substrate.

In these methods, the desired chemical can be an oligopeptide or an oligonucleotide.

DETAILED DESCRIPTION OF THE INVENTION

Figure 1:
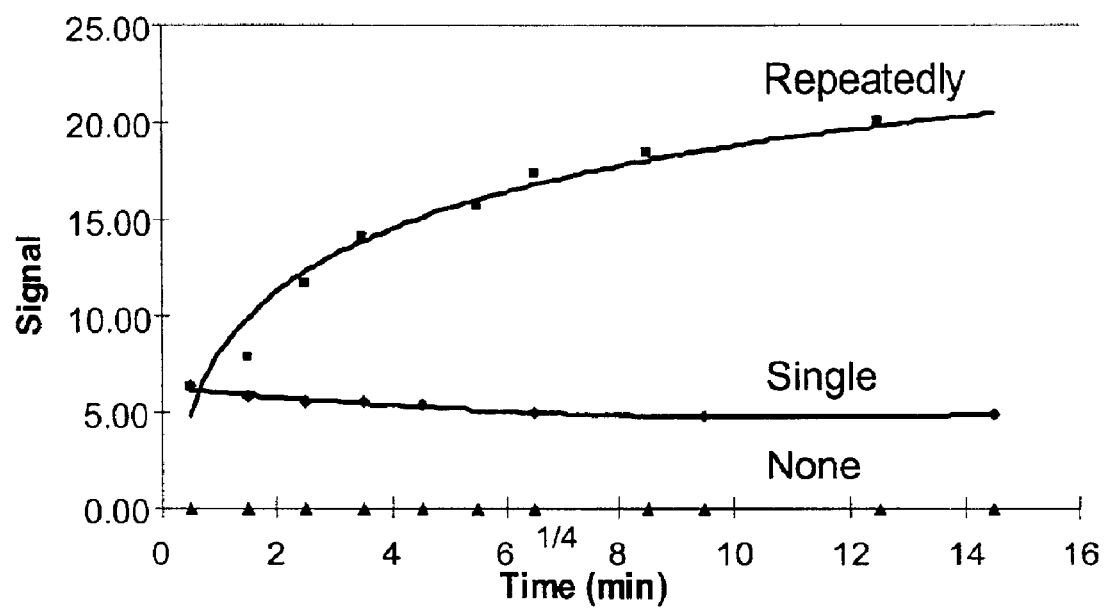
FIG. 1 shows the results for the hybridization assay described in Example 5, which demonstrate that hybridization results can be sampled over time, and that repeated sample application to the substrate results in greater specific binding.

According to various preferred embodiments, when the device of the present invention is useful for performing an assay, the first binding substance is chosen from the group consisting of an oligopeptide, a polypeptide, an oligonucleotide, a polynucleotide, a hapten, and a ligand for a receptor. Nonlimiting examples of these binding substances are nucleic acid probes, antibodies, antigens, receptors, and organic or inorganic chemical compounds.

As used herein, an oligopeptide is a peptide of less than about 30 amino acids, and a polypeptide is a peptide of more than about 30 amino acids. Included herein are peptides with unusual amino acids incorporated, as well as peptide analogs, or peptidomimetics, that are made from amino acid analogs and mimic amino acid chemical characteristics, particularly peptide-peptide interaction characteristics. Peptidomimetics are well known in the art. Also included are molecules comprising a peptide moiety along with other components, such as saccharides, dyes, haptens, etc.

A oligonucleotide, as used herein, is a nucleic acid molecule of less than about 100 nucleotides, and a polynucleotide is a nucleic acid molecule of more than about 100 nucleotides. Also included herein are nucleic acids which incorporate unusual nucleotides, as well as nucleic acid analogs, such as peptide nucleic acids (PNAs), locked nucleic acids, and synthetic nucleic acid binding molecules, such as N-methylimidazole and N-methylpyrrole amino acid sequences that bind in the minor groove of DNA. These analogs are well known in the art. See, e.g., Larsen et al. (1999) Biochem. Biophys. Acta 1489, 159; Wengel et al. (1999) Nucleosides Nucleotides 18, 1365; Braasch et al. (2000) Chem. Biol. 55, 1; Trauger, J. W. et al. (1996) Nature, 382, 559; Nielsen et al. (1991) Science 254, 1497; Wittung et al. (1997) Nucleosid. Nucleotid. 16, 559; U.S. Pat. No. 6,201,103; U.S. Pat. No. 6,204,326. Also included are molecules comprising a nucleotide moiety along with other components, such as saccharides, dyes, haptens, etc.

A hapten is a molecule, preferably organic, that is smaller than about 1000 Dalton. Nonlimiting examples include various enzyme or receptor ligands, antibiotics, organic toxins, and other biologically active molecules.

Assays in which the device according to the present invention can be used include sequencing by hybridisation, immunoassays, receptor/ligand assays and the like.

When the device is used as a tool to obtain DNA sequence information, a large array of areas is provided, each area comprising as a first binding substance an oligonucleotide probe of a different base-pair sequence. If a sample containing DNA or RNA fragments with a (partly) unknown sequence is brought into contact with the substrate a specific hybridisation pattern may occur, from which pattern the sequence information of the DNA/RNA can be derived. Such "sequencing by hybridisation" methods are well known in the art (see e.g. Fodor, S. P. A. et al. (1992) Science 251, 767–773 and Southern, E. M. et al. (1994) Nucleic Acids Res. 22, 1368–1373).

The device according to the present invention may also be used to screen a biological specimen, such as blood, for a large number of analytes. The array may consist of areas comprising oligonucleotide probes or a mix of oligonucleotide probes specific for, for example, *E. coli, S. aureus, S. pneumoniae* etc. A biological sample can be prepared as described in EP 0.389.063, or by any other method known to be useful for preparing samples for such assays. If this sample is brought into contact with the substrate, the resulting hybridisation pattern can be read e.g. using a CCD camera in combination with an appropriate optical marker, or any other method known in the art. Apart from screening for bacteria, the device is suitable for the detection of viruses, as well as the classification of different subtypes of, for example, HIV and HCV etc. Virus classification may be essential to determine potential drug resistance. In general it requires the ability to detect single point mutations, deletions, insertions, etc. in the viral genome.

The device is also suited for performing immunoassays, for instance sandwich immunoassays. In that case, it is preferred that a second antibody is used for binding to bound analyte, said second antibody for each of the analyte being recognised by a third labeled antibody. As is well known in the art, this may be achieved if the second and third antibodies are derived from different species and the third antibody is raised against antibodies of the other species. Thus it is avoided to label the second antibody for each particular analyte. The device is also suited for performing "pepscans" as disclosed in Geysen et al., Proc. Natl. Acad. Sci. USA 81:3998–4002 (1984). In that case the first binding substances that are attached to the different areas of the substrate constitute different sequences of amino acids. If the substrate is brought into contact with a liquid that contains a particular analyte, a reaction pattern enabling affinity analysis by performing fluorescent detection in real-time may occur, representing the specific affinity of the analyte for the different amino acid sequences. This allows the measurement of kinetic curves as illustrated in Examples 6 and 8. It is preferred that the first binding substance is covalently bound to the substrate.

This minimises loss of the first binding substance from the substrate. Covalent binding of an organic compound to a metal oxide is well known in the art, for example using the method described by Chu. C. W., et al. (J. Adhesion Sci. Technol., 7, pp. 417–433, 1993) and Fadda, M. B. et al. (Biotechnology and Applied Biochemistry, 16, pp. 221–227, 1992).

According to a preferred embodiment the metal oxide membrane is comprised of aluminium oxide. Such a membrane of aluminium oxide appears to have through-going channels that are hydrophilic in comparison to the surface of the membrane. Thus, advantageously, a hydrophilic liquid preferably enters the channels instead of spreading over the surface of the membrane. Therefore aluminium oxide membranes can accommodate high densities of areas comprising different first binding substances. Aluminium oxide membranes having oriented through-going channels are disclosed by Rigby, W. R. et al. (Trans. Inst. Metal Finish., 68(3), p. 95, 1990) and are marketed by Anotec Separations Ltd., Oxon, UK. The channels are also interconnected. These membranes have been used to purify viruses, and to store enzymes for sensor purposes, but there is no suggestion with respect to their suitability as substrates for performing probe-based assays.

The present invention also relates to a method of manufacturing a device comprising membranes having oriented through-going channels according to the invention, wherein the first binding substance is synthesised in situ. According to certain aspects of these embodiments, said synthesis includes both chemical as well as enzymatic in situ synthesis. The in situ process based on chemical or enzymatic steps include oligonucleotide and peptide synthesis and enzymatic processes such as pyrosequencing, minisequencing, Invader.

For example, using only a limited number of reagents, for a device comprising an oligonucleotide as the first binding substance usually four nucleotide compounds (dA, dT, dC, and dG for DNA, A, U, C, and G for RNA) and additional reagents such as blocking reagents, and protecting reagents, classical solid phase synthesis techniques can be used to provide a substrate with one or an array of a plurality of areas with oligonucleotide probes. Reagents can conveniently be applied to the through-going channels of a particular area using ink-jet technology. Ink-jet technology allows for the accurate deposition of defined volumes of liquid. In situ synthesis of oligonucleotide probes on a flat, non-porous substrate is well known in the art (see eg. T. P. Theriault: DNA diagnostic systems based on novel Chem-Jet technologies, IBC Conference on Biochip Array Technologies, Washington D.C., May 10, 1995).

According to a preferred embodiment, the nucleotide compounds are applied using electrostatic attraction. Electrostatic attraction diminishes the risk of splattering.

According to an alternative method of manufacturing a device comprising through-going channels according to the invention, the first binding substance is applied to the through-going channels of a particular area using ink-jet technology. This allows for purification of the first binding substance, and for example in case of an oligonucleotide probe for verification of its sequence, before application to the substrate.

For the reasons mentioned earlier, it is again preferred if the first binding substance is applied using electrostatic attraction.

The present invention also relates to a method for the detection of an analyte in a sample comprising the steps of
a) contacting the sample with any of the above described devices,
b) allowing binding to take place between the first binding substance and the analyte, and
c) detecting whether binding has occurred between first binding substance and analyte.

In this method the analyte may be for example an oligopeptide, a polypeptide, an oligonucleotide, a polynucleotide, a hapten, or a ligand for a receptor. Non-limiting examples of these binding substances are nucleic acid probes, antibodies, antigens, receptors, and organic or inorganic chemical compounds.

The use advantageously comprises a nucleic acid hybridisation assay, an immunological assay, a receptor-ligand assay, an enzyme-substrate assay, or any other assay that can usefully utilize the binding characteristics of an analyte and an immobilized binding substance. In such an assay, a sample which comprises an analyte is brought into contact with a device according to the invention. The analyte is subsequently allowed to bind to the first binding substance which is attached to the substrate. Such binding is greatly facilitated by allowing the analyte to migrate through the porous substrate. Detection of binding can be performed by adding a second binding substance attached to a label, allowing said second binding substance to bind to the complex of first binding substance and analyte and determining whether the label is present at the position where the first binding substance was immobilised. Alternatively, the analyte may already have been provided with a label, in which case binding to the first binding substance can be detected directly, without the addition of a second binding substance.

According to a preferred embodiment, a temperature difference is adjusted between different locations on the membrane during performance of the assay to create different hybridisation conditions at different membrane locations.

The ability of varying the temperature in combination with the possibility of performing real-time analysis allows the performance of kinetic analysis. For instance, the effects on changing the temperature on the hybridization of the analyte to different probes, including point mutations, can be measured. By varying the temperature a range of stringency conditions may be obtained, which allows point mutations to be easily distinguished from a perfect match. This is further illustrated in example 7.

The skilled artisan would understand that these assays could utilize the invention device comprising a variety of binding substances, including cDNA arrays, PCR arrays, peptide arrays, oligonucleotide arrays (either presynthesized or synthesized as part of the manufacture of the device), antibody arrays, or protein arrays. Further, essentially any biological assay could be easily adapted for use with the device of the present invention, including assays utilizing PCR, ligase chain reaction (see, e.g., Carrino et al. (1995) J. Microbiol. Meth. 24, 3), nucleic acid sequence-based amplification (NASBA) (see, e.g., Blais et al. (1997) Appl. Environ. Microbiol. 63, 310) including NASBA-fluorescence correlation spectroscopy (see, e.g., Oehlenschlager et al. (1996) Proc. Nat'l. Acad. Sci. USA 93, 12811), self-sustained sequence replication, and Q replicase amplification. The skilled artisan would understand that these assay methods could be used for many purposes. Non-limiting examples include genotyping, including SNP detection and detection of differences larger that single nucleotides (see, e.g., Example 7), gene counting, for example by the MAPH telomeric assay (see, e.g., Sismani et al. (2001) Eur. J. Hum. Genet. 9, 527), antibody epitope mapping, RNA expression profiling, and RNA quantitations (e.g., using NASBA).

The present invention also relates to a kit comprising any of the above mentioned devices, wherein the kit optionally additionally comprises a detection means for determining whether binding has occurred between the first binding substance and the analyte. Preferably, such detection means is a second binding substance provided with a label. Preferably, the label is capable of inducing a colour reaction and or capable of bio- or chemo- or photoluminescence. For instance, the label of the second binding substance may consist of a fluorophore. According to another embodiment, the second binding substance has the format of molecular beacons which are particularly useful for determining particular alleles or single nucleotide variants of nucleic acid sequences in a sample. See, e.g., Marras, S. A. E. et al., (1999) Genet. Anal. Biomol. Eng. 14, 151–156; Tyagi, S. et al. (1996) Nat. Biotechnol. 14, 303–308; Tyagi, S. et al. (1998) Nat. Biotechnol. 16, 49–53. Non-limiting examples of other second binding substances include cyclicons (see, e.g., Kandimalla et al. (2000) Bioorg. Med. Chem. 8, 1911) and light-up probes (see, e.g., Svanvik et al. (2000) Anal. Biochem. 287, 179).

In additional embodiments, the present invention is directed to a device for performing a chemical synthesis. The device comprises a substrate having interconnected channels, said channels opening out on a surface and being oriented essentially perpendicular to the surface for reagent application. The channels in at least one area of the surface for reagent application being provided with a first reacting substance capable of reacting with a second reacting substance, wherein the substrate is an electrochemically manufactured metal oxide membrane and the first reacting substance is within the interconnected channels in the substrate.

The devices of these embodiments are useful for synthesis of oligonucleotides or oligopeptides, or for synthesis of other chemical compounds, using well known solid-phase techniques. With accurate addition of reagents to the interconnected channels, e.g., using ink-jet technology, a series of oligonucleotides or oligopeptides can be prepared which vary slightly in sequence, or combinatorial chemistry methods can be applied to prepare a series of related chemical compounds, which can then be cleaved from the substrate by known methods.

Preferably, the first reacting substance in these methods is a polymer useful for the various synthesis methods, such as any of the resins that are known for this purpose. See, e.g., Merrifield (1985) Angew. Chem. 97, 801; Bunin et al. (1994) Proc. Nat'l. Acad. Sci. USA 91, 4708; Ellman (1996) Account. Chem. Res. 29, 132; Gordon et al. (1994) J. Med. Chem. 37, 1233; Jung et al. (1992) Angew. Chem. Int. Ed. 31, 367; Thompson et al. (1996) Chem. Rev. 96, 555; Bennett (2000), pp. 139–262 in COMBINATORIAL CHEMISTRY: A PRACTICAL APPROACH, H. Fenniri (Ed.), Oxford University Press. These are preferably covalently conjugated to the substrate, by known methods.

Various embodiments of these devices are useful for methods of synthesizing an oligopeptide. See, e.g., Bodanszky (1985) Int. J. Peptide Protein Res. 25, 449. In these embodiments, the methods preferably comprise the following steps:

(a) contact the above device for performing a chemical synthesis with a protected amino acid under conditions and for a time sufficient for the protected amino acid to covalently bind to the polymer;

(b) treat the device to remove the protecting group from the protected amino acid to form a device comprising a polymer covalently bound to a first amino acid; and (c) contact the device comprising a polymer covalently bound to a first amino acid with a second protected amino acid under conditions and for a time sufficient for the second protected amino acid to form a peptide bond with the first amino acid.

As used herein, a "protected" molecule is a molecule with one or more moieties covalently attached to a reactive group to prevent the unwanted reaction of the reactive group with another molecule.

In related embodiments, the above devices for performing a chemical synthesis are also useful for synthesizing an oligonucleotide. See, e.g. Beaucage et al. (1992) Tetrahedron 48, 2223; Vinayak et. al. (1992) Tetrahedron Lett. 31, 7269. These methods preferably comprise the following steps:

(a) contact the device with a protected nucleotide under conditions and for a time sufficient for the protected nucleotide to covalently bind to the polymer;

(b) treat the device to remove the protecting group from the protected nucleotide to form a device comprising a polymer covalently bond to a first nucleotide; and (c) contact the device comprising a polymer covalently bond to a first nucleotide with a second protected nucleotide under conditions and for a time sufficient for the second protected nucleotide to form a phosphodiester bond with the first nucleotide.

In these embodiments, oligodeoxyribonucleotides, oligoribonucleotides, or their analogs can be prepared. The present invention also relates to the use of an electrochemically manufactured metal oxide membrane, preferably an aluminium oxide membrane, in the manufacture of any of the above described devices.

Any of the various methods described herein are generally suitable for adaptation to automation. See, e.g., Cargill et al. (1996) Lab. Robotics. Automation 8, 139; Zuckermann et al. (1992) Int. J. Peptide Prot. Res. 40, 497.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example describes the simultaneous detection of two different types of HIV-1 amplificate, a Wild Type RNA (WT) and a Calibrator RNA (Qa) using an aluminium oxide membrane in a flow through cell.

Analytes

The WT-RNA and the Qa-RNA fragments represent a part from the GAG region of the HIV-1 genome. These fragments have equal lengths (145 nt) and identical sequences, apart from a 21 nt long region in the central part of the fragment. The sequences of the fragments are:

```
WT-RNA:

5'cccugcuaugucacuucccuugguucucucaucuggccuggugcaauaggcccugcaugcacugga    (SEQ ID NO:1)

ugcacucuaucccauucugcagcuuccucauugauggucucuuuuaacauuugcauggcugcuugau gucccсcсacu3'

Qa-RNA:

5'cccugcuaugucacuucccuugguucucucaucuggccuggugcaauaggcccugcaugcgacugu    (SEQ ID NO:2)

caucuaucuacacugucugcagcuuccucauugauggucucuuuuaacauuugcauggcugcuugau gucccсcсacu3'
```

The sequence of the WT and Qa specific parts are underlined.

In this example two buffered solutions were used:

A phosphate buffer at pH 7.4 containing 8 g/l NaCl, ("incubation buffer").

A phosphate buffer at pH 7.4 containing 8 g/l NaCl and 0.05% Polysorbate (Tween 20), hereinafter denoted "wash buffer".

Substrate:

Aluminium oxide membrane, thick 60 µm, diameter 24 mm. Channels are 0.2 µm diameter, density is about 18 channels/µm² ("Anodisc 25", Whatman). The membrane surface was coated with streptavidin by immersing the membrane in the incubation buffer contained 2 g/l streptavidin for 60 min. Subsequently, the membranes were washed using the wash buffer and air dried at room temperature.

Immobilisation of First Binding Substance:

Two oligonucleotide probes, partially complementary to the WT- and QA fragments were applied:

WT-probe: 5'GAATGGGATAGAGTGCATCCAGTG3' (SEQ ID NO:3)

Qa-probe: 5'GACAGTGTAGATAGATGACAGTCG3' (SEQ ID NO:4)

both with a biotin molecule coupled to the 5' end by standard methods.

Spots with a specific diameter were applied using a porous tip (nylon feeder) as found in the common "fineliner" writing pen (Hauser schreibtechnik GmbH,. Gosheim Germany). Whereas the feeder tip spots the membrane, its other end was in fluid contact with a reservoir containing the probe solution (incubation buffer, probe concentration 25 µmol/L). Transfer of probe solution into the membrane was well controlled by the capillary interaction of membrane and feeder: the probe solution autonomously filled up those channels that were in physical contact with the feeder tip. In this example 2 lines with 3 spots of 0.5 mm diameter have been used (3 spots for each probe type). The distance between individual spots was 1 mm. After spotting and an incubation phase of 10 min at room temperature, unbound probe material was washed away using the wash buffer.

In this example, 4 identical substrates were produced in this way.

Hybridisation:

Next, the membranes were introduced in a flow through cell and brought into contact with the incubation buffer containing the HIV RNA fragments. Four sets of hybridisation conditions have been applied in 4 different experiments:

1 volume 25 µl containing 1.5×10¹² molecules of QA RNA, no flow 2 volume 25 µl containing 1.5×10¹² molecules of WT RNA, no flow 3 volume 25 µl containing 1.5×10¹² molecules of QA RNA, continuous flow 4 volume 25 µl containing 1.5×10¹² molecules of WT RNA, continuous flow With experiment 1 and 2 there was no transport of the buffer through the membrane.

With experiment 3 and 4, the 25 µl RNA solution continuously flowed through the membrane in two directions (back and forth) with a velocity of about 25 µl/min.

To control this flow, an automated Hamilton dispenser was used. With all experiments hybridisation was at room temperature during 10 min.

Washing:

After hybridisation the membranes were washed using 5 ml of the wash buffer.

Labeling and Detection:

For detection, a probe that is generic for HIV RNA (SEQ ID NO:5) was allowed to interact with the membranes. This probe was contained in the incubation buffer (40 nmol/L). In each experiment a volume of 75 µl was used, without flow. The probes were labeled with the horseradish peroxidase (HRP) enzyme in a 1:1 ratio, using maleimide containing heterobifunctional cross-linkers (Hashida, S., et al. (1984) J.Applied Biochem. 56, 56–63). Prior to the HRP coupling the probes were thiolated (Carlsson, J., et al. (1978) Biochem. J. 173, 723–737). After washing with 10 ml wash buffer, a solution containing 3,3',5,5'-tetramethylbenzidine hydrogenperoxide (TMB) (Organon Teknika, art: 78510), was brought into contact with the membranes (no flow).

Results:

Interpretation of the results was with the unaided eye. In experiment 3 and 4, blue spots appeared almost immediately at a location where a specific reaction was expected (spots containing WT probes turned blue using WT-RNA and spots containing Qa probes turned blue using Qa-RNA). With the spots containing probes that were not complementary to the RNA in the buffer no colouring was observed, although the area on the membrane in between the spots showed a slight bluish colour after several minutes, probably due to insufficient washing or some non specific binding. In experiment 1 and 2 a similar result was obtained, however, in these cases it took about a minute before blue spots became visible.

In addition to the visual evaluation of the spots during the TMB reaction, the spots on the membranes in experiments 3 and 4 were evaluated using an imaging densitometer (Biorad GS700). To this end the membranes were removed from the flow-through cells (Table 1).

TABLE 1

Density of spots measured with densitometer

| RNA analyte | spot with WT-probes (OD units) | spot with Qa-probes (OD units) | background area (OD units) |
|---|---|---|---|
| WT-RNA | 38 | 20 | 20 |
| Qa-RNA | 25 | 35 | 25 |

EXAMPLE 2

Oligonucleotide probes were covalently coupled to the Anopore membranes using 3-aminopropyl triethoxysilane (APS) as a linker between the alumina and the oligo. For the experiments Anodics 25 membranes with a diameter of 25 mm and a total surface area of 0.3 m² were used. The membranes were activated by immersion in a nitric acid solution (0.4 mol/l) for 1 hour. After rinsing with water the membranes were dried and immersed in a 0.25% (v/v) solution of APS in water for 2 hours. Excess APS was removed by rinsing with water. After drying at 120° C. at reduced pressure the membranes were stored. Amino group concentration due to the coupling of the APS molecules was typically 2–3 $\mu mol/m^2$.

Before coupling, the amino group-terminated oligonucleotides were activated by reaction with disuccinimidyl suberate (DSS, see eg. PIERCE BV, Immunotechnology Catalog & Handbook, 1990). The resulting succinimidyl group at the end of the oligonucleotide was used for coupling to the APS activated membrane. Labeling with $^{32}P$ was used for quantification of the results. Coupling with 500 $\mu l$ oligo solution on an Anodisc membrane during 60 minutes resulted in a coupling yield of $110^{-10}$ mol/m² oligonucleotide.

EXAMPLE 3

This example describes the definition of an array pattern on an $Al_2O_3$ membrane using an ink-jet device. Using standard ink-jet technology small droplets having a diameter of 20–80 $\mu m$ could be generated and positioned on a substrate at high throughput rates and at $\mu m$ resolution. Using a commercially available desk-jet (HP 660C) in combination with the $Al_2O_3$ membranes arrays of a very high resolution were obtained. Visual inspection with a microscope (magnification: 400×) shows perfectly round spots of approximately 60 $\mu m$ diameter having very sharp margins. No signs of splattering, as is commonly observed when using non-porous surfaces, was observed. We attribute the high array resolution to the high porosity of the material in combination with the hydrophilic character of the through-going channels.

EXAMPLE 4

This Example describes a sandwich immunoassay utilizing aspects of the present invention. Specifically, the detection of human chorionic gonadotrophin (hCG) with an enzyme immunoassay using an aluminium oxide membrane as solid phase is described.

Coating of the Membrane:

Small areas of aluminium oxide membranes (round with a diameter of 20 mm) were coated with a buffered solution (0.0127 mol/l phosphate and 0.140 mol/l NaCl at pH 7.4) containing 1 $\mu g/ml$ monoclonal mouse antibody (OT-hCG-4B) directed against hCG. The solution was applied by pipetting 10 $\mu l$ droplets onto the membrane or by contact spotting using a polyester feeder (Hauser). After incubation at 37° C. for 30 minutes the membranes were ready for use.

Incubation:

The positive samples were a mixture of 50 $\mu l$ hCG with a concentration of 2000 IU/l and 50 ul mouse anti-hCG (OT-hCG-3A) conjugated with horseradish peroxidase (HRP) (1 $\mu g/ml$). This mixture was pre-incubated for 15 minutes. In the case of the negative control 50 $\mu l$ buffer was mixed with 50 $\mu l$ conjugate solution. Next, the mixture (100 $\mu l$) was pipetted onto the membranes and incubated for 15 minutes at room temperature.

Washing and Detection:

The membranes were extensively rinsed with a washing buffer (0.131 mol/l NaCl, 0.0127 mol/l phosphate and 0.5 ml/l Polysorbate 20) on a funnel. Finally the membranes were placed in a beaker containing a substrate for HRP based on 3,3',5,5'-tetramethylbenzydine and hydrogen peroxide (Organon Teknika). During 30 minutes incubation the results were observed visually and with a camera.

Results:

Clear blue spots became visible within a few minutes where the membranes were coated with OT-hCG-4B in the case of the positive samples. On the other parts of the membrane and with the negative control only a faint blue background colour could be observed after a relatively long incubation.

EXAMPLE 5

This example illustrates the repeated measurement of signal development in a nucleic acid hybridization assay using various conditions for hybridization.

Binding:

The membrane was prepared with oligonucleotides as outlined in Example 2.

Hybridization:

The membrane was then introduced in a flow through cell and brought into contact with a fluorescent-labeled complementary probe as outlined in Example 1.

Detection:

Detection was performed on a fluorescent microscope (Olympus Optical). Spot density was recorded from the images using a commercial software package (Paintshop pro) and plotted against time. Results are illustrated in FIG. 1. With repeated binding of the complementary oligonucleotide, a binding isotherm was constructed. When only a single binding step was used (i.e., the sample was passed through the membrane only once), no further increase was observed. No signal was generated when no sample was passed through the membrane.

EXAMPLE 6

This example illustrates the repeated measurement of signal development in an immunoassay of immobilized peptides.

Preparation:

The membrane was prepared with a set of six peptides (Pepscan, The Netherlands).

Binding:

The membrane was then introduced in a flow through cell and brought into contact with an antibody complex at 37° C. Prior to this step, the complex was formed by a 60 min. incubation at 37° C. of (a) an antibody (Pepscan) at 1.9 g/l, and (b) a goat anti-mouse antibody labeled with fluorescein at 1.3 g/l (Pierce, The Netherlands), in 1× PBS (Roche, The Netherlands). The Pepscan antibody is known to have different affinities for the peptides. Before use, the complex was diluted in PBS/Tween (Organon, The Netherlands) to a final concentration of 0.5 mg/l.

The flow through cell is temperature controlled to 37° C. The 20 μl solution was passed through the membrane four times per minute. After 30 minutes of incubation a new 20 μl sample of the diluted antibody-complex was added to the same well of the aluminium holder and incubation was continued.

Detection:

After each passage of the sample, the fluorescence was recorded with a fluorescent microscope (Olympus Optical) and digitized with a CCD camera (Kappa, The Netherlands). The image information was converted into spot intensity values using a MatLab software image analysis package (Pamgene, Dan Bosch, The Netherlands).

Figure 2:
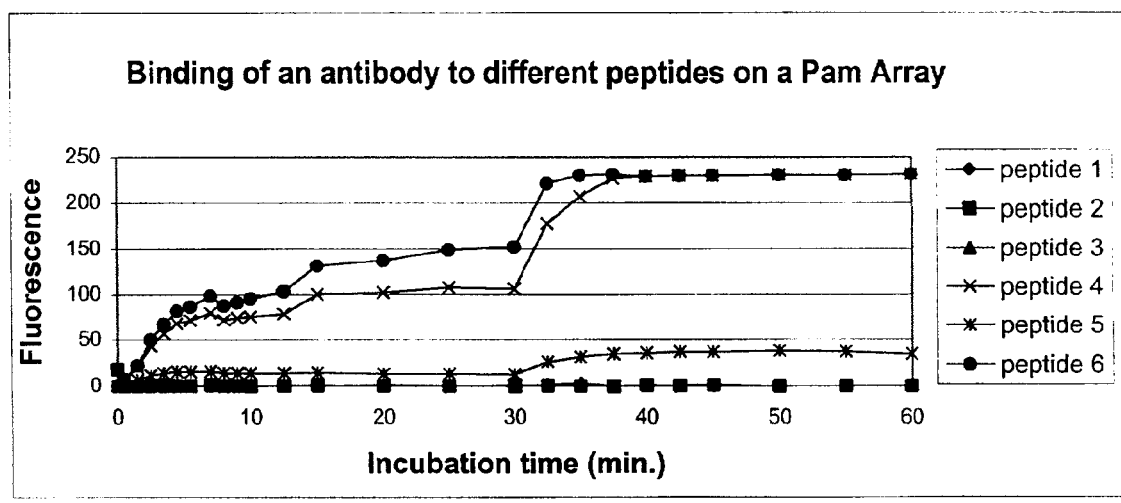
FIG. 2 shows the results of a PepScan immunoassay using the methods of the present invention, demonstrating that differing binding affinities can be discerned.

Results:

The results of this assay is illustrated in FIG. 2, which shows the fluorescence intensity values for each peptide after 0, 0.5, 1.5, 2.5, 3.5, 4.5, 5.5, 7, 8, 9, 10, 12.5, 15, 20, 25, 30, 32.5, 37.5, 40, 42.5, 45, 50, 55, and 60 min. This demonstrates that antibody binding data can be obtained over time. FIG. 2 shows that the antibody has different affinities for the tested peptides, with peptides 1, 4, and 5 having highest to lowest affinity ranking, and the other peptides (2, 3 and 6) showing no antibody binding. After 20–30 minutes all antibodies in the solution are bound to the peptides. The addition of fresh solution after 30 min increases the signal values.

EXAMPLE 7

This example illustrates variations in the amount of hybridization of a probe with bound oligonucleotides, when the bound oligonucleotides have varying amounts of sequence mismatches with the probe.

Binding:

The membrane was prepared with a set of 21-mer oligo-nucleotides (SEQ ID NO:6–21) (Isogen, The Netherlands) as outlined in Example 2. The list of oligonucleotides is shown in Table 2.

fluorescent-labeled complementary probe having several to no mismatches with the membrane bound oligonucleotides. The flow through cell was temperature controlled. The 25 μl solution as described in Example 1 was passed through the membrane twice per minute, which equals one step in FIG. 3.

Detection:

After each passage of the sample, the fluorescence was recorded with a fluorescent microscope (Olympus Optical) and digitized with a CCD camera (Sony, Japan). The image formation was converted into spot intensity values using a MatLab software image analysis package (Pamgene, Dan Bosch, The Netherlands).

Figure 3:
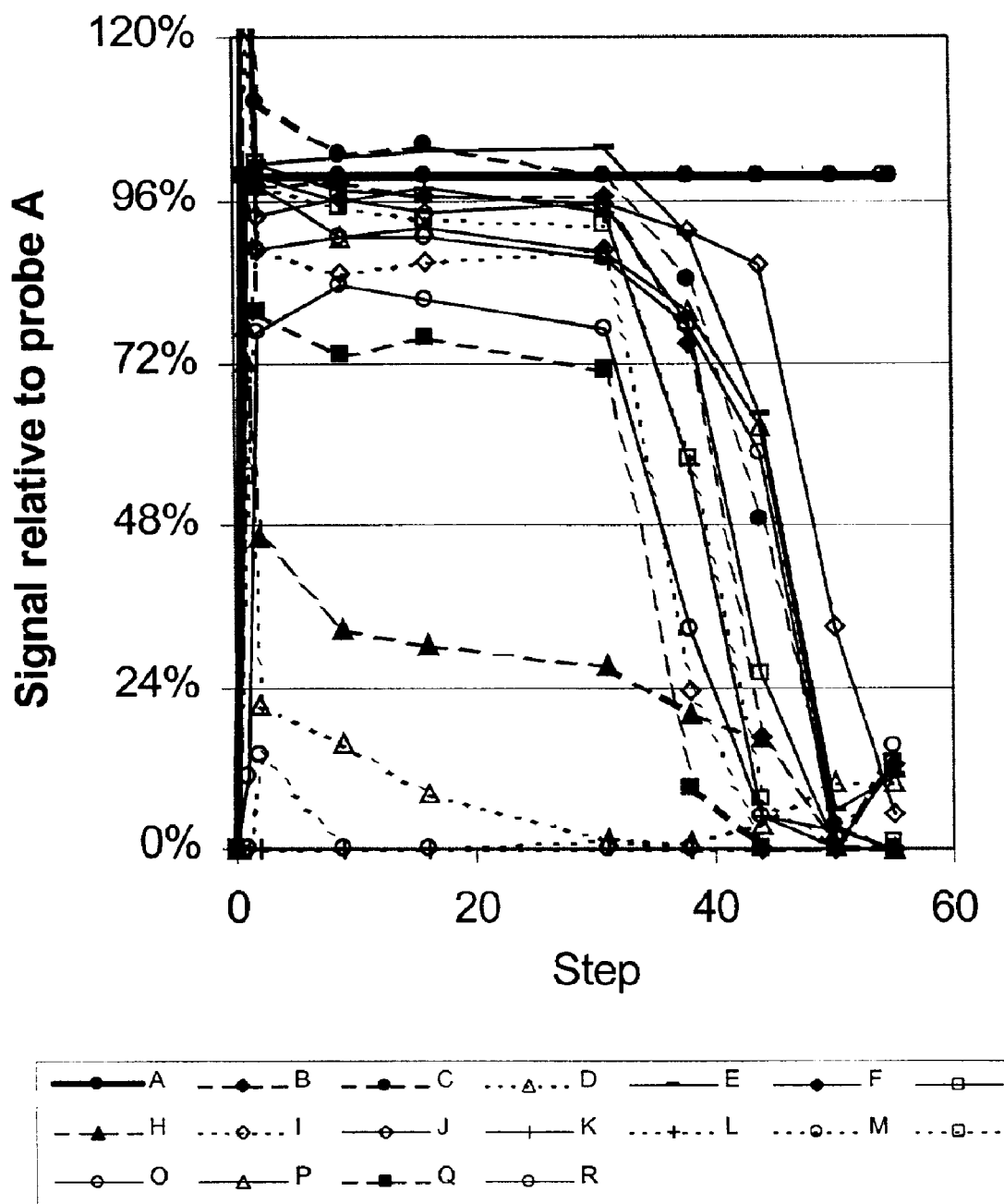
FIG. 3 shows the results of an oligonucleotide hybridization assay using the methods of the present invention, demonstrating that different stringencies of hybridization can be evaluated on a single membrane and that repeated hybridization steps can increase the ability of the assay to discern degrees of homology between the bound oligonucleotide and an oligonucleotide in the sample.

Results:

The result of the binding is illustrated in FIG. 3, after 0, 1, 2, 9, 16, 31, 38, 44, 50 and 55 minutes. The signal increased from 0 to 31 minutes as a function of time. As shown in FIG. 3, the specificity of the binding is increased by changing the temperature at times 38, 44, 50 and 55 minutes from 25° C. up to respectively 48, 54, 60 and 63° C. This is shown as signal intensity values of the perfect match spot A (SEQ ID NO:6) compared to spots B-R (SEQ ID NO:7–21, respectively, except for control spot F). Increasing the temperature up to 48° C. and higher increases the specificity and therefore the signal difference between the perfect match and single or multiple mismatches. At 63° C. the signal of the perfect match is discriminated from all other single mismatches by a factor of four.

EXAMPLE 8

This example compares PepScan analyses using a traditional method with the method of the present invention.

The membrane was prepared with a set of 20-mer peptides (ABL, Kensington USA) with 16 amino acid overlap covering the sequence part of the V3 loop of HIV1. The same method as shown in Example 6 was used to preform a "PepScan" analysis on a mouse monoclonal antibody to HIV-1 gp 120 (Organon Teknika, The Netherlands). As a reference the procedures for PepScan analysis were per-

TABLE 2

Sequences of the 21-mer oligonucleotides. Both the D. Negative control, and the F. Fluorescent control are of unrelated sequences to the target. The positive control is used to focus the fluorescent microscope.

```
Probe No. T T G T A C A G A A A T G G A A A A G G A  Mismatches

A         - - - - - - - - - - - - - - - - - - - - -   0
B         - - - - G - - - - G - - - - - - - - - - -   2
C         - - - - - A - - - - - - - - - C - - - - -   2
D. Negative control - unrelated sequence
E         - - - - C - - - - - - - - - - - - - - - -   1
F. Fluorescent control - unrelated sequence
G         - - - - - - - - - - C - - - - - - - - - -   1
H         - - - - T T - - - - - - - - - - - - - - -   2
I         - - - - G - - T T T - - - - - G G - - - -   6
J         - - - - G - - - - - - - - - - - - - - - -   1
K         - - - - - - - - - - - - - C - - - - - - -   1
L         C C A - T G - C - G - A - A - - - - A T -  11
M         - - A A T A - - - G - A C T C - - G A C T  13
N         - - - - - A - - - G - - - - - - - C - - -   3
O         - - - - - - - - - - - G - - - - - - - - -   1
P         - - - - - - - - - - - - - - - - G - - - -   1
Q         - - - - - - - - - - C - - - - G - - - - -   2
R         - - - - - - - - - - - T - - - - - - - - -   1
```

Next, the membranes were introduced into the flow through cell and brought into contact with 10 nM of a formed with slight modifications (Goudsmit J et al., 1989, J. Med. Primatol 18, 357–362).

Figure 4:
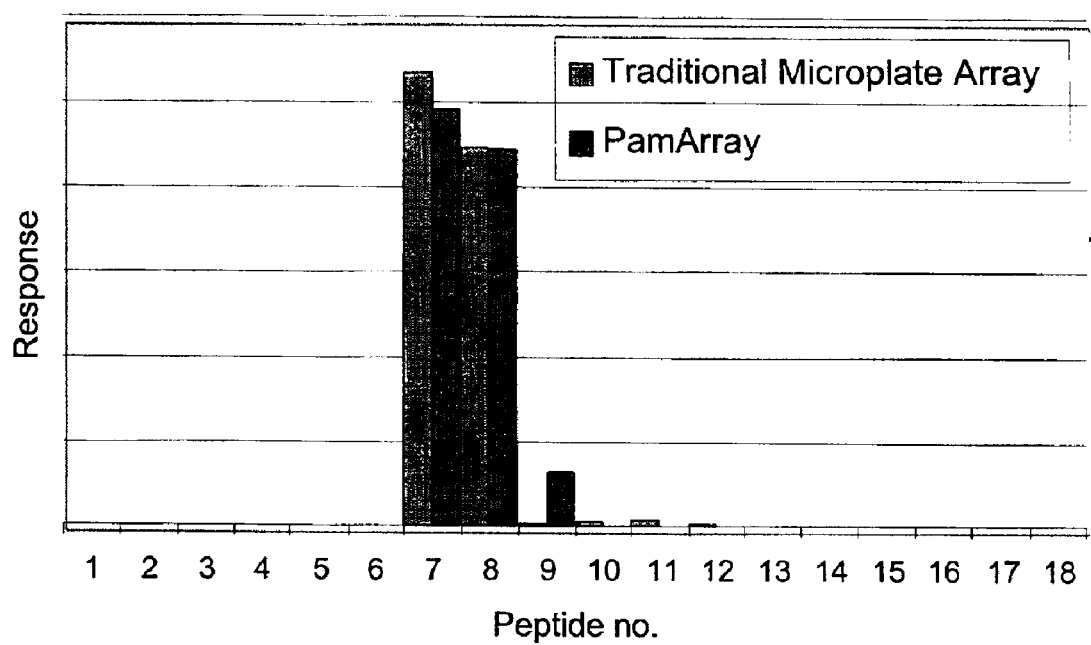
FIG. 4 shows a comparison of a PepScan using the invention method with a PepScan using a traditional method, showing that the invention method can provide results similar to the traditional method.

FIG. 4 shows the results of this experiment. There is a close comparison between the traditional PepScan method and the method of the present invention. Thus, the method of the invention enables affinity analysis using a peptide array. Such methods would also be understood to be useful for antibody epitope analysis.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A device for performing an assay, which device comprises a substrate having interconnected channels, said channels opening out on a surface for sample application, the channels in at least one area of the surface for sample application being provided with a first binding substance capable of binding to an analyte, wherein the substrate is an electrochemically manufactured metal oxide membrane and the first binding substance is within the interconnected channels in the substrate.

2. The device of claim 1, wherein the metal oxide membrane is comprised of aluminium oxide.

3. The device of claim 1, wherein the first binding substance is covalently bound to the substrate.

4. The device of claim 1, wherein the first binding substance is selected from the group consisting of an oligopeptide, a polypeptide, an oligonucleotide, a polynucleotide, a hapten, and a ligand for a receptor.

5. The device of claim 4, wherein the first binding substance is an oligopeptide.

6. The device of claim 5, wherein the oligopeptide comprises an immunogenic epitope.

7. The device of claim 5, wherein the oligopeptide comprises a portion of an HIV protein.

8. The device of claim 4, wherein the first binding substance is a polypeptide.

9. The device of claim 8, wherein the first binding substance is an antibody or an enzyme.

10. The device of claim 4, wherein the first binding substance is an oligonucleotide.

11. The device of claim 10, wherein the first binding substance comprises a portion of an HIV genome.

12. A kit comprising (a) the device of claim 1, and (b) a detection means for determining whether binding has occurred between the first binding substance and the analyte.

13. The kit of claim 12 wherein the detection means comprises a second binding substance provided with a label.

14. The kit of claim 13, wherein the label is capable of inducing a colored or infrared or ultraviolet reaction product, or capable of bio- or chemo- or photoluminescence.

15. The kit of claim 14, wherein the detection means uses an enzymatic reaction.

16. A device for performing a chemical synthesis, which device comprises a substrate having interconnected channels, said channels opening out on a surface, the channels in at least one area of the surface for reagent application being provided with a first reacting substance capable of reacting with a second reacting substance, wherein the substrate is an electrochemically manufactured metal oxide membrane and the first reacting substance is within the interconnected channels in the substrate.

17. The device of claim 16, wherein the first reacting substance is a polymer.

18. The device of claim 16, wherein the first reacting substance is covalently bound to the substrate.

19. The device of claim 17, wherein the polymer is capable of covalently binding to an organic molecule of less than 1000 Dalton.

20. The device of claim 17, wherein the polymer is capable of covalently binding to a modified amino acid useful for oligopeptide synthesis.

21. The device of claim 17, wherein the polymer is capable of covalently binding to a modified nucleotide useful for oligonucleotide synthesis.

* * * * *

UNITED STATES PATENT AND TRADEMARK OFFICE
CERTIFICATE OF CORRECTION

| | | |
|---|---|---|
| PATENT NO. | : 6,855,539 B2 | Page 1 of 1 |
| APPLICATION NO. | : 09/997213 | |
| DATED | : February 15, 2005 | |
| INVENTOR(S) | : Hendrik Sibolt van Damme et al. | |

It is certified that error appears in the above-identified patent and that said Letters Patent is hereby corrected as shown below:

Title page

Item (73), Assignee, "PamGene International B.V." should read --PamGene B.V.--.

Signed and Sealed this

Eleventh Day of September, 2007

JON W. DUDAS
*Director of the United States Patent and Trademark Office*